United States Patent
Austin et al.

(10) Patent No.: US 11,537,748 B2
(45) Date of Patent: Dec. 27, 2022

(54) SELF-CONTAINED SYSTEM FOR DE-IDENTIFYING UNSTRUCTURED DATA IN HEALTHCARE RECORDS

(71) Applicant: Datavant, San Francisco, CA (US)

(72) Inventors: Joseph Austin, Sterling, MA (US); Shahir Kassam-Adams, Lovingston, VA (US); Jason A. LaBonte, Natick, MA (US); Paul J. Bayless, Burke, VA (US)

(73) Assignee: Datavant, Inc., San Francisco, CA (US)

( * ) Notice: Subject to any disclaimer, the term of this patent is extended or adjusted under 35 U.S.C. 154(b) by 1010 days.

(21) Appl. No.: 16/255,443

(22) Filed: Jan. 23, 2019

(65) Prior Publication Data

US 2019/0236310 A1 Aug. 1, 2019

Related U.S. Application Data

(60) Provisional application No. 62/622,677, filed on Jan. 26, 2018.

(51) Int. Cl.
*G06F 21/62* (2013.01)
*G16H 10/60* (2018.01)

(52) U.S. Cl.
CPC ......... *G06F 21/6254* (2013.01); *G16H 10/60* (2018.01)

(58) Field of Classification Search
CPC ............................ G06F 21/6254; G16H 10/60
See application file for complete search history.

(56) References Cited

U.S. PATENT DOCUMENTS

| | | |
|---|---|---|
| 5,892,900 A | 4/1999 | Ginter et al. |
| 6,397,224 B1 | 5/2002 | Zubeldia et al. |
| 6,732,113 B1 | 5/2004 | Ober et al. |
| 6,734,886 B1 | 5/2004 | Hagan et al. |
| 6,804,787 B2 | 10/2004 | Dick |
| 7,120,928 B2 | 10/2006 | Sheth et al. |
| 7,269,578 B2 | 9/2007 | Sweeney |
| 7,376,677 B2 | 5/2008 | Ober et al. |
| 7,428,706 B2 | 9/2008 | Hagan et al. |
| 7,519,591 B2 | 4/2009 | Landi et al. |
| 7,526,485 B2 | 4/2009 | Hagan et al. |
| 7,543,149 B2 | 6/2009 | Ricciardi et al. |

(Continued)

FOREIGN PATENT DOCUMENTS

WO    WO 2009/010718 A1    1/2009

OTHER PUBLICATIONS

Final Office Action from U.S. Appl. No. 15/045,605, dated Nov. 4, 2019.

(Continued)

*Primary Examiner* — Kristine L Kincaid
*Assistant Examiner* — Lydia L Noel
(74) *Attorney, Agent, or Firm* — Morse, Barnes-Brown & Pendleton, P.C.; Sean D. Detweiler, Esq.

(57) ABSTRACT

A method and apparatus for identifying personally identifiable information (PII) and protected health information (PHI) within unstructured data, removing the PII and PHI from the unstructured data, and replacing the removed information with case-type tags that allows the user to understand what information was removed and to tune the level of information removal in future data sets.

18 Claims, 7 Drawing Sheets

(56) References Cited

U.S. PATENT DOCUMENTS

| | | |
|---|---|---|
| 7,587,366 B2 | 9/2009 | Grim, III et al. |
| 7,668,835 B2 | 2/2010 | Judd et al. |
| 7,711,120 B2 | 5/2010 | Kimmel et al. |
| 7,792,517 B2 | 9/2010 | Mowry et al. |
| 7,827,234 B2 | 11/2010 | Eisenberger et al. |
| 7,865,376 B2 | 1/2011 | Ober et al. |
| 7,945,048 B2 | 5/2011 | Ricciardi et al. |
| 8,024,339 B2 | 9/2011 | Barker et al. |
| 8,037,052 B2 | 10/2011 | Kariathungal et al. |
| 8,042,193 B1 | 10/2011 | Piliouras |
| 8,069,053 B2 | 11/2011 | Gervais et al. |
| 8,090,595 B2 | 1/2012 | Hartman |
| 8,121,984 B2 | 2/2012 | Barbieri et al. |
| 8,176,334 B2 | 5/2012 | Vainstein |
| 8,275,850 B2 | 9/2012 | Kohan et al. |
| 8,296,299 B2 | 10/2012 | Haskell et al. |
| 8,296,341 B2 | 10/2012 | Hagan et al. |
| 8,341,427 B2 | 12/2012 | Auradkar et al. |
| 8,355,923 B2 | 1/2013 | Gervais et al. |
| 8,364,969 B2 | 1/2013 | King |
| 8,381,287 B2 | 2/2013 | Trotter |
| 8,473,452 B1 | 6/2013 | Ober et al. |
| 8,494,874 B2 | 7/2013 | Green, III et al. |
| 8,560,456 B2 | 10/2013 | Williams |
| 8,566,113 B2 | 10/2013 | Friedlander et al. |
| 8,577,933 B2 | 11/2013 | Evenhaim |
| 8,589,437 B1 | 11/2013 | Khomenko et al. |
| 8,656,161 B2 | 2/2014 | Nakae |
| 8,661,249 B2 | 2/2014 | Guarraci et al. |
| 8,683,552 B2* | 3/2014 | Nonaka .................. G06F 21/62 726/28 |
| 9,292,707 B1 | 3/2016 | Fontecchio |
| 9,614,814 B2 | 4/2017 | Fontecchio |
| 9,734,169 B2* | 8/2017 | Redlich .................. G06Q 10/10 |
| 9,830,476 B2 | 11/2017 | Fontecchio |
| 9,928,379 B1 | 3/2018 | Hoffer |
| 9,977,775 B2* | 5/2018 | Cougias ................ G06F 40/295 |
| 10,129,370 B2 | 11/2018 | Levy et al. |
| 10,200,397 B2* | 2/2019 | Dhar .................. G06F 16/3334 |
| 10,255,456 B2 | 4/2019 | Guglani et al. |
| 10,305,911 B1* | 5/2019 | Eyre ...................... H04L 63/102 |
| 10,713,390 B2 | 7/2020 | Anderson et al. |
| 10,891,610 B2 | 1/2021 | Powell et al. |
| 10,902,081 B1 | 1/2021 | Gassner et al. |
| 10,910,089 B2 | 2/2021 | Austin et al. |
| 10,984,128 B1 | 4/2021 | Hoffer |
| 11,004,548 B1 | 5/2021 | Austin et al. |
| 11,042,668 B1 | 6/2021 | Kassam-Adams et al. |
| 11,080,423 B1 | 8/2021 | Kassam-Adams et al. |
| 11,081,219 B1 | 8/2021 | Dods et al. |
| 11,120,144 B1 | 9/2021 | Kassam-Adams et al. |
| 11,127,491 B2 | 9/2021 | Austin et al. |
| 11,222,139 B2 | 1/2022 | Jones et al. |
| 2002/0073138 A1 | 6/2002 | Gilbert et al. |
| 2002/0173971 A1 | 11/2002 | Stirpe et al. |
| 2003/0061482 A1 | 3/2003 | Emmerichs |
| 2006/0053032 A1 | 3/2006 | Weiler et al. |
| 2007/0067626 A1 | 3/2007 | Briancon et al. |
| 2007/0162377 A1 | 7/2007 | Williams |
| 2007/0255704 A1* | 11/2007 | Baek .................. G06F 21/6254 |
| 2008/0003964 A1 | 1/2008 | Alperin et al. |
| 2008/0147554 A1 | 6/2008 | Stevens et al. |
| 2009/0106550 A1 | 4/2009 | Mohamed |
| 2009/0287502 A1 | 11/2009 | Roberts et al. |
| 2010/0042583 A1 | 2/2010 | Gervais et al. |
| 2010/0070306 A1 | 3/2010 | Dvorak et al. |
| 2010/0094758 A1 | 4/2010 | Chamberlain et al. |
| 2010/0114607 A1 | 5/2010 | Kress et al. |
| 2010/0205009 A1 | 8/2010 | Kostoff |
| 2010/0211781 A1 | 8/2010 | Auradkar et al. |
| 2010/0223467 A1 | 9/2010 | Dismore et al. |
| 2010/0256994 A1 | 10/2010 | Eisenberger et al. |
| 2011/0191245 A1 | 8/2011 | Ricciardi et al. |
| 2012/0036360 A1 | 2/2012 | Bassu et al. |
| 2012/0116800 A1 | 5/2012 | McCallie et al. |
| 2012/0124637 A1 | 5/2012 | Dunaway |
| 2012/0159637 A1 | 6/2012 | Dove et al. |
| 2012/0173884 A1 | 7/2012 | Patil |
| 2012/0204032 A1 | 8/2012 | Wilkins et al. |
| 2012/0226916 A1 | 9/2012 | Hahn et al. |
| 2012/0303558 A1 | 11/2012 | Jaiswal |
| 2012/0316898 A1 | 12/2012 | Levitt et al. |
| 2013/0117126 A1 | 5/2013 | Coppinger |
| 2013/0117128 A1 | 5/2013 | Coppinger |
| 2013/0167192 A1* | 6/2013 | Hickman ............ G06F 21/6245 726/1 |
| 2013/0246097 A1 | 9/2013 | Kenney et al. |
| 2013/0304504 A1 | 11/2013 | Powell |
| 2013/0304542 A1 | 11/2013 | Powell |
| 2013/0346104 A1 | 12/2013 | Pillai |
| 2014/0013452 A1 | 1/2014 | Aissi et al. |
| 2014/0040308 A1 | 2/2014 | Ober et al. |
| 2014/0041047 A1 | 2/2014 | Jaye et al. |
| 2014/0108049 A1 | 4/2014 | Fuhrmann et al. |
| 2014/0108258 A1 | 4/2014 | Williams |
| 2014/0122873 A1 | 5/2014 | Deutsch et al. |
| 2015/0086020 A1 | 3/2015 | Harjula et al. |
| 2015/0089357 A1 | 3/2015 | Vandervort et al. |
| 2015/0095243 A1 | 4/2015 | Eiler et al. |
| 2015/0095252 A1 | 4/2015 | Mattsson et al. |
| 2015/0149208 A1 | 5/2015 | Lynch et al. |
| 2016/0110648 A1 | 4/2016 | Baveja et al. |
| 2016/0147945 A1 | 5/2016 | MacCarthy et al. |
| 2016/0267238 A1 | 9/2016 | Nag |
| 2016/0275309 A1 | 9/2016 | Austin et al. |
| 2016/0344544 A1 | 11/2016 | Biesinger et al. |
| 2017/0103179 A1 | 4/2017 | Jiao et al. |
| 2017/0243028 A1 | 8/2017 | LaFever et al. |
| 2019/0138698 A1 | 5/2019 | Qiu |
| 2019/0236310 A1 | 8/2019 | Austin et al. |
| 2021/0012332 A1 | 1/2021 | Ow et al. |
| 2021/0065267 A1 | 3/2021 | Smith et al. |
| 2021/0081366 A1 | 3/2021 | Madisetti et al. |
| 2021/0182423 A1 | 6/2021 | Padmanabhan |
| 2021/0248268 A1 | 8/2021 | Ardhanari et al. |
| 2021/0256070 A1 | 8/2021 | Tran et al. |
| 2021/0263971 A1 | 8/2021 | Landes |
| 2021/0319436 A1 | 10/2021 | Ow et al. |
| 2021/0350891 A1 | 11/2021 | Dods et al. |
| 2022/0050921 A1* | 2/2022 | LaFever .............. H04L 63/0407 |
| 2022/0172809 A9* | 6/2022 | Lyman .................. G16H 40/67 |

OTHER PUBLICATIONS

Non-Final Office Action from U.S. Appl. No. 16/382,447, dated Dec. 16, 2020.
Non-Final Office Action from U.S. Appl. No. 15/045,605, dated Feb. 13, 2020.
Notice of Allowance for U.S. Appl. No. 16/684,541, dated Jun. 8, 2021.
Notice of Allowance for U.S. Appl. No. 16/382,428, dated May 27, 2021.
Final Office Action for U.S. Appl. No. 15/045,605, dated May 8, 2020.
Notice of Allowance for U.S. Appl. No. 15/045,605, dated Oct. 14, 2020.
Non-Final Office Action for U.S. Appl. No. 16/382,462, dated Oct. 29, 2020.
Non-Final Office Action 15/045,605, dated Jul. 18, 2019.
Third Party Submission Under 37 CFR 1.290 for U.S. Appl. No. 15/045,605, made/submitted Mar. 29, 2019.
Notice of Allowance for U.S. Appl. No. 16/135,972, dated Jan. 28, 2021.
Non-Final Office Action for U.S. Appl. No. 16/684,541, dated Feb. 18, 2021.
Notice of Allowance for U.S. Appl. No. 16/382,462, dated Mar. 3, 2021.
http://mist-deid.sourceforge.net/ "MIST—The MITRE Identification Scrubber Toolkit".
Non-Final Office Action from U.S. Appl. No. 16/135,972, dated Aug. 13, 2020.

(56) References Cited

OTHER PUBLICATIONS

Notice of Allowance from U.S. Appl. No. 16/382,447, dated Apr. 12, 2021.
Final Office Action from U.S. Appl. No. 17/464,246, dated Jul. 6, 2022.
Non-Final Office Action for U.S. Appl. No. 17/464,246, dated Mar. 28, 2022.

* cited by examiner

SELF-CONTAINED SYSTEM FOR DE-IDENTIFYING UNSTRUCTURED DATA IN HEALTHCARE RECORDS

CROSS-REFERENCE TO RELATED APPLICATION(S)

This application claims priority to, and the benefit of, co-pending U.S. Provisional Application No. 62/622,677, filed Jan. 26, 2018, for all subject matter common to both applications. The disclosure of said provisional application is hereby incorporated by reference in its entirety.

FIELD OF THE INVENTION

The present invention relates to identifying personally identifiable information (PII) and protected health information (PHI) within unstructured data, removing the PII and PHI from the unstructured data, and replacing the removed information with a case-type tag. In particular, the present invention relates to a system and method configured to provide an improvement in computer capabilities that enables a computer system to merge data sets without compromising data privacy and security that computers were not capable of performing before using existing data replication techniques, by de-identifying (removing PII and/or PHI) found within unstructured data fields, such as physician notes, laboratory results, and medical histories, from public and private sources, etc. and replacing the removed personal information with a case-type tag that enables the user to understand what information was removed and to tune the level of information removal in future de-identification runs.

BACKGROUND

There exists a vast store of information within the unstructured data fields of healthcare records that can be critical to properly understanding the effectiveness and safety of clinical treatment. However, due to their inherent lack of structure, de-identification of these data fields is a challenge due to the lack of an automated solution, leaving much of this information absent from analytical datasets. This challenge is one that was created by the implementation of databases and other data storage and analysis technologies combined with the unstructured nature of healthcare records combined with the need for meeting privacy regulations and requirements. Conventional healthcare data systems are limited in their ability to provide information from individual records in healthcare data sets because each record contains protected health information ("PHI") or personal identification information (PII) (e.g., names, addresses, dates of birth, dates of death, social security numbers, etc.). It is a potential Health Insurance Portability and Accountability Act (HIPAA) violation to incorporate PHI elements into a healthcare data set. Accordingly, to be compliant with government regulations, all PHI data elements must be removed and/or de-identified before being incorporated into any healthcare data set. However, once PHI data elements are removed from record, users have no way to understand which individuals in the data set match particular structured or unstructured data relevant for analysis.

Generally, conventional (systems, devices, methods) are unable to identify, flag, and remove protected health information (PHI) or personal identification information (PII) (e.g. names, addresses, dates of birth, dates of death, social security numbers, etc.) from unstructured data in an automated fashion. Instead, the current practice is to remove PHI or PII manually based on human determinations, or to not incorporate any unstructured data fields into healthcare data sets being used for non-clinical purposes, because of the inability to efficiently and accurately identify, flag, and remove PHI or PII using existing technologies.

SUMMARY

There is a need for improvements for enabling healthcare data sets within healthcare records of individuals to be accessible and useable without exposing protected healthcare information of the individual. There is a need for improvements for a system whereby unstructured data can be de-identified in an automated manner, but still be able to be matched to individual records in healthcare data sets without exposure of PHI or PII. Additionally, the de-identification process needs to be "tune-able" to control redaction of sensitive information while allowing information that looks like PHI or PII, but is not, to remain in the data set. Moreover, it would be desirable to have the de-identified text to remain coherent after the personal identifying information has been removed.

The present invention is directed toward further solutions to address this need, in addition to having other desirable characteristics. Specifically, the present invention provides an advancement made in computer technology that consists of improvements defined by logical structures and processes directed to a specific implementation of a solution to a problem in software, data structures and data management, wherein the existing data structure technology relies upon unacceptable reproduction of protected health information, personal identification information, or other private information to transmit data for data processing purposes that cannot meet or be used under current requirements of the Health Insurance Portability and Accountability Act (HIPAA) (42 U.S.C. § 1301 et seq.), and other laws, regulations, rules and standards governing privacy and data security (e.g. General Data Protection Regulation (Regulation (EU) 2016/679), Federal Trade Commission Act (15 U.S.C. §§ 41-58), Children's Online Privacy Protection Act (COPPA) (15 U.S.C. §§ 6501-6506), Financial Services Modernization Act (Gramm-Leach-Bliley Act (GLB)) (15 U.S.C. §§ 6801-6827) and California Consumer Privacy Act of 2018), by providing a system and method in which unstructured data is processed from individual records in a healthcare data set without exposing PHI. The present invention provides a system and method that creates a specific, non-abstract improvement to computer functionality previously incapable of merging certain data sets without exposing PHI and PII, that de-identifies data by removing protected health information and personal identification information from the record, adds a unique encrypted person token to each record, and merges the record with other healthcare data sets that have likewise been de-identified and tokenized by matching the unique encrypted person tokens in data sets to one another, thus maintaining the ability to match disparate data (e.g., unstructured data and structured healthcare data) from disparate sources for a same individual. In particular, the present invention implements a self-contained, dictionary-based system containing tunable lists of PHI or PII entities and data formats (e.g., names, birth dates, phone numbers, addresses, etc.) to be utilized to de-identify unstructured data within healthcare and other data sets. The dictionaries include blacklisted terms (e.g., first names, last names, etc.) to be redacted from the unstructured data and also include blacklisted standard number formats (e.g., social security numbers, telephone numbers, etc.) to be removed from records, a project specific whitelist of terms not to be removed (terms to be allowed to remain in the data despite being included in the blacklist), and a record-specific blacklist created from the PHI or PII present in a specific record (e.g., individual patient records). Taken together, these three dictionaries create an adjusted blacklist that can be "tuned" to control the level of de-identification and scrub a set of records. The present invention uses the dictionaries to remove all elements determined to be PII or PHI, but also replaces the removed elements with a case-type tag identifying the type of information being removed (e.g., "first name", "address", etc.). The addition of the case-type tag ensures that the unstructured data are still coherent even after information has been removed/redacted.

Additionally, to connect the resulting de-identified data to other data sets, the invention works in a manner consistent with other de-identification systems and methods. In particular, the records are tokenized in a standardized format to include encrypted patient tokens with every record. This "tokenized" data can then be merged with structured healthcare data sets that have also been de-identified and tokenized by matching the tokens in each data set against each other. In this way, users can connect individuals across healthcare data sets without ever seeing or using PHI or PII.

In accordance with example embodiments of the present invention, a method for de-identifying unstructured data within data sets is provided. The method includes initializing a blacklist dictionary and a whitelist dictionary, modifying the blacklist dictionary by removing terms included within the whitelist dictionary to create an adjusted blacklist dictionary, and augmenting the adjusted blacklist dictionary with a record-specific blacklist for each individual record within the data sets. The method also includes scrubbing personally identifiable information (PII) and protected health information (PHI) from each individual record utilizing the record-specific adjusted blacklist dictionary. The scrubbing includes removing all elements within each individual record determined to be PII or PHI according to terms in the record-specific adjusted blacklist dictionary, replacing removed elements with a case-type tag identifying a type of information being removed according to the record-specific adjusted blacklist dictionary, and repeating the removing and replacing step for each individual record within the data sets.

In accordance with aspects of the present invention, the method can further include tokenizing and merging each individual record in the data sets. The blacklist dictionary can include standard terms and standard number formats to be removed from records within the data sets. The standard number formats can include social security numbers, telephone numbers, URLs, zip codes, email addresses, IP addresses, dates, patient IDs, record numbers, and insurance IDs. The standard formats can include cities, counties, first names, last names, prefixes, and medical terms. The whitelist dictionary can include terms allowed to remain in the data sets despite being included in the blacklist dictionary. The record-specific adjusted blacklist dictionary can include terms created from the PII or PHI present in specific individual records within the data sets.

In accordance with aspects of the present invention, the method can further include tuning terms in the whitelist dictionary and the record-specific adjusted blacklist dictionary to adjust a level of de-identification of records within the data sets. The whitelist dictionary and the record-specific adjusted blacklist dictionary can include a tunable list of names, birth dates, phone numbers, addresses and other forms of PII and PHI. Augmentation can include adjusting the adjusted blacklist dictionary to include known PII and PHI terms for an individual associated with an individual record, according to the record-specific adjusted blacklist dictionary, that should be removed.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to a system and process for providing automated de-identification of unstructured data within health records. The present invention utilizes a dictionary-based and format-based engine to identify PHI and PII information for removal. The dictionaries can include tunable de-identification parameters through the use of a whitelist and standard and record-specific blacklist dictionaries to ensure that the correct information is being flagged as PHI or PII while not incorrectly flagging information needed for a particular analysis. The combination of the standard blacklist, customizable whitelist, and record-specific blacklists allow users to tune which terms they wish to obfuscate or pass through the de-identification process. Other de-identification methods for unstructured data do not include this element of tuneability.

The specific system and method improve the existing technology by reciting specific structures, functions and steps that accomplish the desired result through an inventive arrangement by combining unstructured data with other healthcare data in a manner that does not violate HIPAA or other privacy related regulations that restrict PHI or PII. In particular, unstructured data is accessed or aggregated from different data sources and is de-identified by removing or modifying all elements regarded as protected health information, and a unique encrypted person token is added to each record. The "tokenized" data is merged with other healthcare data sets that have been de-identified and tokenized in a similar process, that uses a combined order of specific incorporated rules and functions, not mere use of the computer and existing data processing technology, that improves the existing data management technological processes that renders unstructured data and health care information into a specific format that is then used and applied to create desired results of data sets that can be used together in an encrypted and privacy preserving manner. Specifically, the healthcare data sets are merged with the unstructured data by matching the unique encrypted person tokens associated with each data record with one another and the data records with matching unique encrypted person tokens are merged together. Using the system and method of the present invention provides a specific, non-abstract improvement to computer functionality that enables "individuals" (e.g., de-identified healthcare records) in a healthcare data set to be supplemented with unstructured data that is tunable without exposing protected health information or personal identification data. This in turn enables databases or data structures containing health care data sets, operated by separate, potentially unrelated entities, to query, receive, and incorporate (including by merging) data sets including unstructured data or related data in a separate database or data structure that ordinarily would not be capable of interacting due to the above discussed restrictions on combining such data and the existing technological requirements of reproducing data within data structures in order to preserve unique identifiers and data used to accurately correlate or match data based on association with an underlying entity.

The data sets, used or created by the present invention, contain the de-identified unique encrypted person tokens, an indicator of the individual previously identified in the data record, and tag data including case-type tag data. This transformed data functions differently than, and achieves benefits over, conventional database structures and data therein, providing increased flexibility, and the ability to combine otherwise un-combinable data sets. To improve accuracy without sacrificing privacy and data security, data sets provide encrypted person tokens that are unique to a particular individual. Once the data sets and healthcare data sets are merged, a user can perform analysis of anonymous healthcare data with the added benefit of the case-type tags indicating what type of data was removed or replaced for the de-identified individuals originally associated with the healthcare records. This functionality provides many added benefits not previously available to healthcare practitioners. For example, unstructured data is critical to properly understanding the effectiveness and safety of clinical treatment. Additionally, the present invention can be utilized to prevent identity theft, fraud, and similar negative occurrences by reducing transmission and retention of versions of data containing PII and PHI. The de-identification of healthcare data sets including unstructured data sets provided by the present invention enables additional data to be merge-able with the healthcare data sets in such a way that data sets from disparate sources but relating to a same individual can be matched up and associated with each other without the exposure of PHI. More specifically, the present invention utilizes the dictionaries to identify PHI or PII information, remove it, and add back a case-type tag (e.g. [name]) in place of the removed information. This combination of dictionaries provides a wide array of standard terms that are commonly associated with PHI or PII as well as a customizable whitelist of terms that may provide false positives for PHI or PII. The present invention allows modification of the standard list with the customized list to ensure the most accurate automated de-identification process. In particular, because the list of terms utilized by the automated system can be finely tuned to specific applications (e.g., healthcare records) and even specific records (e.g., a specific patient record), it can provide a process which will remove all PHI or PII while keeping terms that may look like PHI or PII when viewed without context (e.g., disease names like Parkinson's) but are not PHI or PII. This ensures that the right information is removed (PHI or PII) while not unnecessarily removing other non-protected information (e.g., false positives).

Additionally, by providing tags for removed information, the process of the present invention provides a record that is clear of PHI or PII while maintaining a level of coherency with the tags providing context to the removed text. More specifically, when removing PHI or PII, the present invention replaces these elements with a case-type tags (such as [First Name], [Address], etc.) so that the reader of the resulting de-identified data can determine the type of data that was removed. The inclusion of these case-type tags makes the de-identified data more legible, and allows the user to better tune the system (by seeing what information was removed).

FIGS. 1 through 7, wherein like parts are designated by like reference numerals throughout, illustrate an example embodiment or embodiments of improved operation for the de-identification of PHI and PII within unstructured data sets, according to the present invention. Unstructured data sets can include any collection of data that is not organized in a structured manner. For example, unstructured data sets can include collections of data such as a physician's notes, narrative text (e.g., dictated report, typed findings, etc.), or any data that are not stereotypical, conventionally arranged, and/or predictable. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed in a manner still in keeping with the spirit and scope of the present invention.

Figure 1:
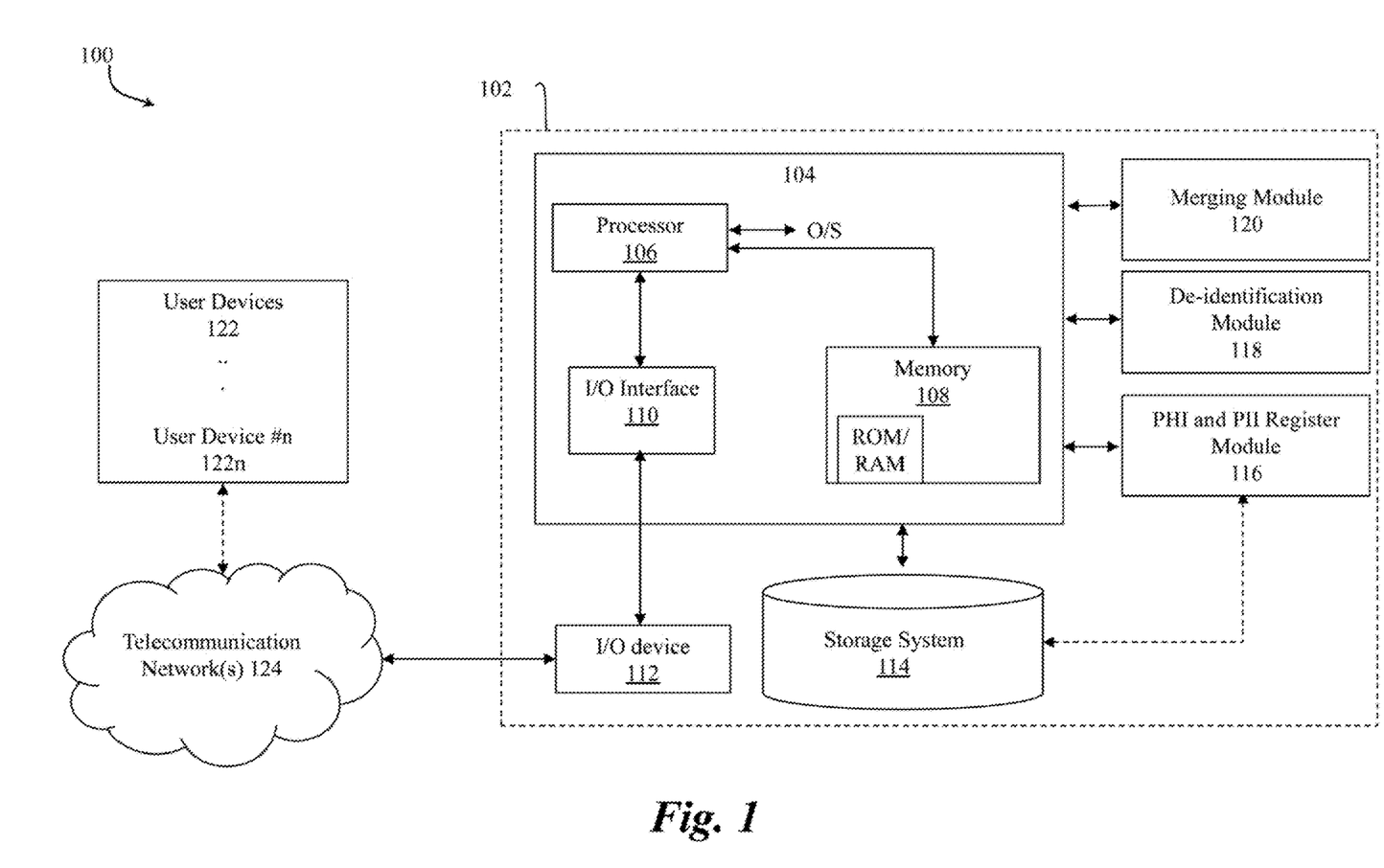
FIG. 1 is a diagrammatic illustration of a system for implementation of the present invention.

FIG. 1 depicts an illustrative system 100 for implementing the steps in accordance with the aspects of the present invention. In particular, FIG. 1 depicts a system 100 including a de-identification engine 102 configured to provide the de-identification of unstructured data. The system 100 is also configured to tokenize the de-identified data and merge the tokenized data with de-identified data created from structured data sets. In accordance with an example embodiment, the de-identification engine 102 is a combination of hardware and software configured to carry out aspects of the present invention. In particular, the de-identification engine 102 is a computing system with specialized software and databases designed for providing a method for de-identifying and tokenizing unstructured healthcare records. For example, the de-identification engine 102 can be software installed on a computing device 104, a web-based application provided by a computing device 104 which is accessible by computing devices (e.g., the user devices 122), a cloud based application accessible by computing devices, or the like. The combination of hardware and software that make up the de-identification engine 102 are specifically configured to provide a technical solution to a particular problem utilizing an unconventional combination of steps/operations to carry out aspects of the present invention. In particular, the de-identification engine 102 is designed to execute a unique combination of steps to provide a novel approach to automatically removing PHI and PII from unstructured data sets/records.

In accordance with an example embodiment of the present invention, the de-identification engine 102 can include a computing device 104 having a processor 106, a memory 108, an input output interface 110, input and output devices 112 and a storage system 114. Additionally, the computing device 104 can include an operating system configured to carry out operations for the applications installed thereon. As would be appreciated by one skilled in the art, the computing device 104 can include a single computing device, a collection of computing devices in a network computing system, a cloud computing infrastructure, or a combination thereof. Similarly, as would be appreciated by one of skill in the art, the storage system 114 can include any combination of computing devices configured to store and organize a collection of data. For example, storage system 114 can be a local storage device on the computing device 104, a remote database facility, or a cloud computing storage environment. The storage system 114 can also include a database management system utilizing a given database model configured to interact with a user for analyzing the database data.

Continuing with FIG. 1, the de-identification engine 102 can include a combination of core components to carry out the various functions of the present invention. In accordance with an example embodiment of the present invention, the de-identification engine 102 can include a PHI and PII register module 116, a de-identification module 118, and a merging module 120. As would be appreciated by one skilled in the art, the PHI and PII register module 116, the de-identification module 118, and the merging module 120 can include any combination of hardware and software configured to carry out the various aspects of the present invention.

In accordance with an example embodiment of the present invention, the system 100 can include a plurality of user devices 122 configured to communicate with the de-identification engine 102 over a telecommunication network(s) 124. The de-identification engine 102 can act as a centralized host, for the user devices 122, providing the functionality of the modules 116, 118, 120, sharing a secured network connection. As would be appreciated by one skilled in the art, the plurality of user devices 122 can include any combination of computing devices, as described with respect to the de-identification engine 102 computing device 104. For example, the computing device 104 and the plurality of user devices 122 can include any combination of servers, personal computers, laptops, tablets, smartphones, etc. In accordance with an example embodiment of the present invention, the computing devices 104 and 122 are configured to establish a connection and communicate over telecommunication network(s) 124 to carry out aspects of the present invention. As would be appreciated by one skilled in the art, the telecommunication network(s) 124 can include any combination of known networks. For example, the telecommunication network(s) 124 may be combination of a mobile network, WAN, LAN, or other type of network. The telecommunication network(s) 124 can be used to exchange data between the computing devices 104, 122, exchange data with the storage system 114, and/or to collect data from additional sources.

In accordance with an example embodiment of the present invention, the PHI and PII register module 116 manages a standard blacklist and whitelist stored and managed by the system 100 (e.g., on storage system 114). Each of the blacklists and whitelist contain lists of entities acting as definitions for identifiable words, terms, phrases, numeric sequences, etc. The standard blacklist contains a predetermined list of commonly defined entities that should be removed in accordance with protected health information (PHI) and personal identification information (PII). For example, the blacklist can include defined entities for names for individuals (first and last), street addresses, dates, social security numbers, etc. As would be appreciated by one skilled in the art, the blacklist can include an aggregated set of restricted terms according to PHI and PII rules and restrictions in any combination of data sets and data configurations. For example, the entities in the blacklist can be represented by lists of each entity organized in categories (e.g. a list of all known names, a list of all known phone numbers or, alternatively, phone number formats, etc.). Although the standard blacklist contains a predetermined list of defined entities, it can be modified by adding or removing individual words, terms, phrases, numeric sequences, numeric formats, etc. within the categorized lists or by adding/or removing entire lists of entities. Moreover, each of the entities can include multiple formats. For example, a social security number can be represented as 123456789, 123-45-6789, etc.

In accordance with an example embodiment of the present invention, the whitelist is a user-defined list of defined entities that should permitted to be included within a data set in accordance with PHI or PII rules and regulations. For example, permitted entities could include, but are not limited to, a list of all disease names, numerical disease codes, etc. As would be appreciated by one skilled in the art, the whitelists can also utilize different dictionary sources including but not limited to medical and healthcare dictionaries and databases. The words, terms, phrases, numeric sequences, etc. included within the whitelist are entities that should be removed or modified within excluded words, terms, phrases, numeric sequences, etc. included within the predefined entities in the standard blacklist. In other words, the whitelist is an aggregation of entity lists that can be utilized by the PHI and PII register module 116 and are provided to modify the standard blacklist when the lists of entities included therein are too comprehensive such that they may remove elements in the data sets which are not actual PHI or PII. Thus, to mitigate over comprehensive issues, the customizable whitelist is used to define the specific terms and elements that are not to be removed from data sets, even if they are included in the standard blacklist.

Similar to the blacklist, the whitelist can include categorized lists of entities. Moreover, as would be appreciated by one skilled in the art, the entities in the lists for the blacklists and whitelists can include any combination of case-sensitivity, not case-sensitive, exact matches, partial matches, etc. Additionally, the entities in the blacklist and whitelist can be drawn and updated from fixed lists or from real-time data sources. Entities in these lists can be updated with information from a variety of data sources (e.g., government databases, public records, etc.) with new data (e.g., such as new birth announcements, zip codes, addresses, etc.) as it becomes available.

FIGS. 2-4 and 6 show illustrative flow charts depicting implementation of the present invention. As would be appreciated by one skilled in the art, the individual steps in any of the flow charts can be performed through different techniques, and/or merged into single processes or split into smaller processes that can be run serially or in parallel. Likewise, the combination of steps represented by the flow charts themselves can be performed through different techniques, and/or merged into single processes or split into smaller processes that can be run serially or in parallel.

Figure 2:
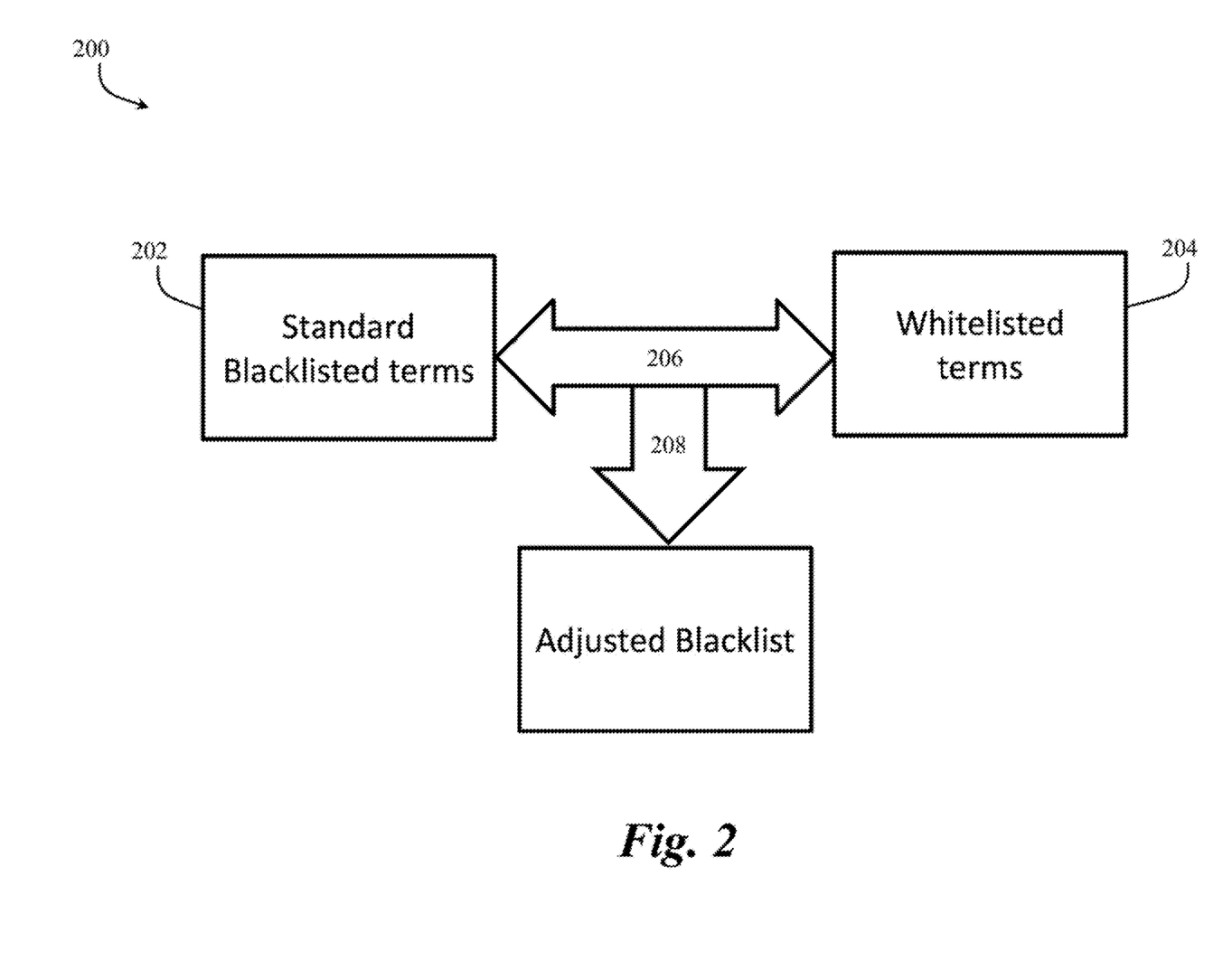
FIG. 2 is a flow chart illustrating how the standard blacklist is combined with the whitelist to generate an adjusted blacklist.

FIG. 2 depicts an exemplary process 200 for configuring tunable entity lists for the de-identification of data sets. In particular, FIG. 2 depicts how the PHI and PII register module 116 is utilized to modify a standard blacklist with a customized whitelist to generate an adjusted blacklist for use by the de-identification module 118. Upon completion of the process 200, the adjusted blacklist can be utilized by the de-identification module 118 to determine which unstructured elements are to be removed from a data set.

At step 202 of the process 200, the PHI and PII register module 116 loads the list of entities from the blacklist. At step 204 the PHI and PII register module 116 loads the list of entities from the whitelist. As would be appreciated by one skilled in the art, the blacklist and whitelist can be loaded from any combination of local or remote storage devices. At step 206, the PHI and PII register module 116 identifies the terms that are included within both the blacklist and the whitelist. For example, the PHI and PII register module 116 runs a comparison operation and caches all entities (e.g., terms, phrases, etc.) found in both lists. At step 208, the terms identified in step 206 are removed from the entity lists included in the standard blacklist. By removing the terms identified in step 206 from the standard blacklist, these entities will be preserved within the data sets during the de-identification process.

As shown in FIG. 2, the result of step 208 (e.g., removing the whitelisted entities from the standard blacklist entities) is the generation of an adjusted blacklist. The adjusted blacklist can be tuned to remove more or less information during the subsequent de-identification process by modifying the elements that are contained in the whitelist (and in some instances the standard blacklist). In ideal conditions, the adjusted blacklist will be tuned to specific data set types such that it will include entities that are PHI or PII while removing terms that may be false positives in that type of data set. For example, in medical-related data sets, the term "Parkinson" can be identified as a name to be removed per the standard blacklist, however, the phrase "Parkinson's Disease" can be defined as an allowed term per the whitelist. In the process 200 depicted in FIG. 2, the combination of the standard blacklist and the whitelist would result in the term "Parkinson" not being present in the adjusted blacklist (e.g., designated for removal). Thus, the adjusted blacklist can be utilized to more accurately remove PHI and PII without removing data that may not be PHI and PII (e.g., Parkison's disease) but is critical information to maintain in the record. Accordingly, the process 200 of combining a standard blacklist with a user-defined whitelist enables a customizable, and more importantly, a tunable degree of de-identification. The combination of, and customizable nature of, the standard blacklist and the whitelist gives users a much higher level of control over the de-identification process than is currently available for unstructured data. Additionally, the use of these lists over a manual process de-identification process makes the system more automatic, more accurate, and more predictable in repeated results. The results of the process 200 can be analyzed to tune the effectiveness of the de-identification process. In particular, as results are provided, the results can be analyzed to determine if too much or too little PHI or PII has been removed and the blacklist and whitelist can be adjusted accordingly (e.g., "tuned"). Tuning incorporates risk tolerance profiles, and can be done by a user who is reviewing the results and assessing what level of risk they are desirous of accepting.

Figure 3:
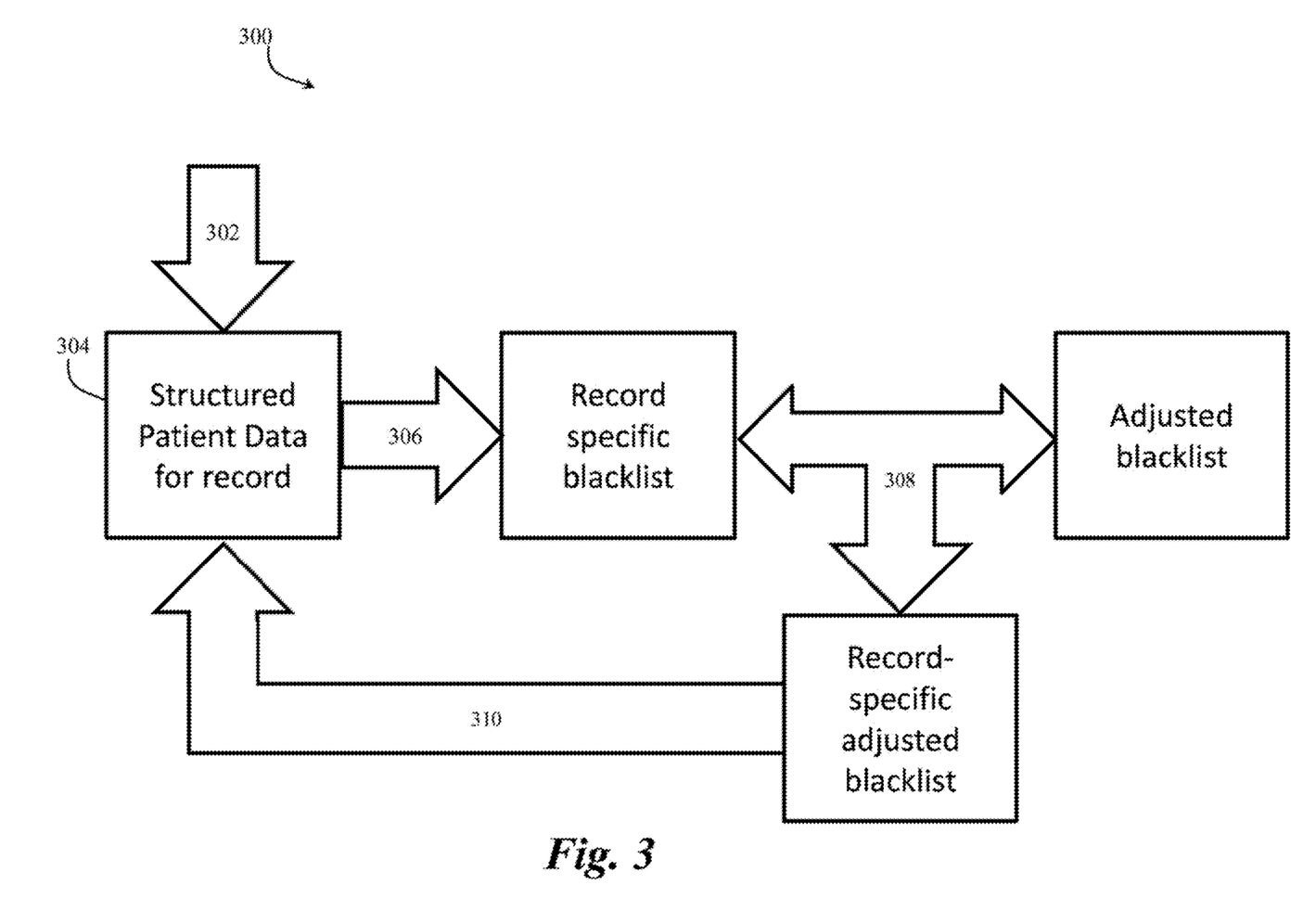
FIG. 3 is a flow chart illustrating the relationship between structured patient data, the creation of a record-specific blacklist, and its addition to the adjusted blacklist for use on that record.

In accordance with an example embodiment of the present invention, the adjusted blacklist can be further adjusted on a per-record basis. FIG. 3 depicts an exemplary process 300 for the augmentation of the adjusted blacklist with a record-specific blacklist. The process 300 for augmenting the adjusted blacklist is an additional independent process from the process 200 in FIG. 2 because the process 300 is performed on a per record basis within a data set to more finely tune the data while the process 200 is performed at a data set level. In particular, regardless of the entities that are designated as "allowed" to remain in the adjusted blacklist, per the whitelist and process 200 in FIG. 2, the entities that are known to be PHI or PII for an individual associated with a specific record must be removed. In other words, the process 200 is the initial part of an overall process that includes running both the process 200 and process 300 in succession.

At step 302 of the process 300, structured patient data records for specific individuals are loaded by the system 100. As would be appreciated by one skilled in the art, the structured patient data record can be a record populated with data for a specific individual patient and can be populated through any combination of manual data entry and automatic processes. Because the PHI and PII information in structured data sets are easier to identify, the structured data sets for an individual can be leveraged to further tune the blacklist to be utilized in unstructured data sets. For example, birth dates can be differentiated from other dates in free text by understanding which field in the structured data set contains the birth date. Likewise, patient names can be differentiated from physician names in unstructured data by understanding which fields in the structured data contain those elements. Extraction of the values from these identified PII and PHI fields in the structured data creates a record-specific blacklist.

At step 304 the PHI and PII register module 116 scans for a structured patient data record for a specific individual. As would be appreciated by one skilled in the art, the specific unstructured data record must be tied to a specific structured data record for this process 300 to work. For example, the records can be linked through a record ID number, a patient ID number, an encrypted token, etc.

At step 306, if there is a structured patient data record for the specific individual, the PHI and PII register module 116 extracts PHI and PII entity data from the structured patient data record and creates a record-specific blacklist for the individual with that entity information. For example, the record-specific blacklist will include words, terms phases, etc. such as the name, birth date, addresses, phone numbers, etc., of the individual.

At step 308 the PHI and PII register module 116 adds the entities from the record-specific blacklist and the adjusted blacklist from process 200 into a single record-specific adjusted blacklist for the record associated with the individual. The record-specific adjusted blacklist defines the complete set of entities to be removed from the unstructured data in that specific record. For example, continuing the previous example, the term "Parkinson" was not removed from unstructured data because, though it looks like a name and may be contained in the standard blacklist, it is an allowed disease term per the whitelist. In the event that the individual record being de-identified, however, contains the term "Parkinson" in its structured data as PHI or PII (perhaps as a name, e.g. "John Parkinson"), the term "Parkinson" will be added to a record-specific blacklist and thus will be removed from the unstructured data in that particular record regardless of its whitelist status (e.g., because it is identifiable information for that particular individual). Implementing the additional structured patient data for a record the system 100 of the present invention accounts for record-specific details that impact the de-identification process. In other words, supporting this type of record-specific customization generates more accurate and flexible automatic de-identification of unstructured data by taking into account record-specific variations.

At step 310, upon completion of the de-identification process on that record (discussed in greater detail with respect to FIGS. 4, 5, and 6 below), the adjusted blacklist for the specific record (generated at step 308) is discarded. In particular, the record-specific entities added as a result of steps 306 and 308 are dropped, and the process 300 is repeated for the next record.

Figure 4:
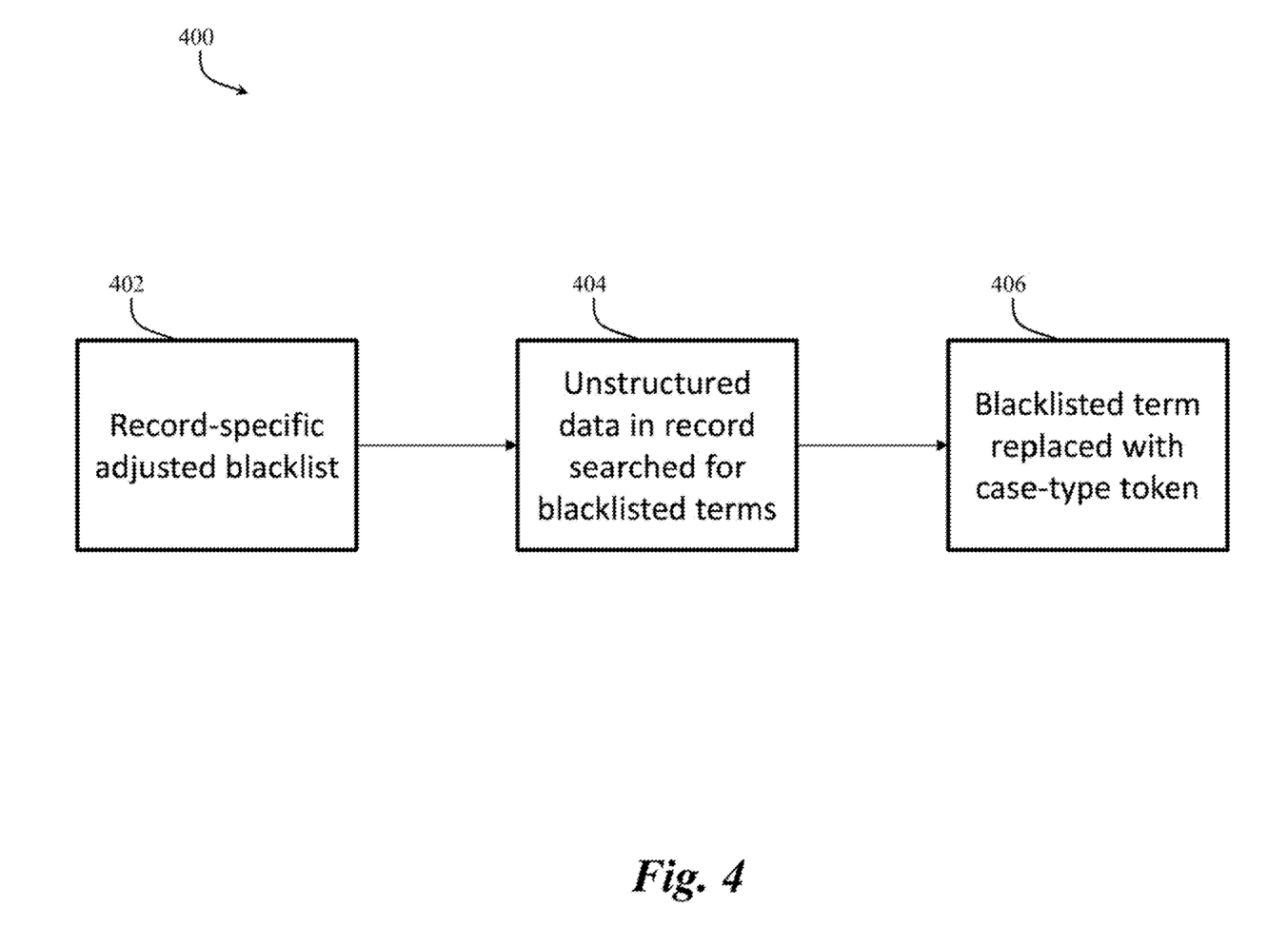
FIG. 4 is a flow chart illustrating how the adjusted blacklist for the record is applied to the unstructured patient record data to generate the de-identified, tokenized record.

FIG. 4 illustrates the process 400 by which the de-identification module 118 performs de-identification on the unstructured data records (e.g., patient records) utilizing the record-specific adjusted blacklist. Initially, at step 402 the de-identification module 118 receives the record-specific adjusted blacklist for the specific individual's record from the process 300 (e.g., the result of step 308).

At step 404 the de-identification module 118 scans through the unstructured data fields within an individual record, identifies and flags entities that are included in the record-specific adjusted blacklist. For example, the system 100 can search through the text using identifying predefined fields of data and data formats.

At step 406 each flagged protected health information entity is removed from the unstructured data record and replaced with a case-specific tag (e.g. [name]). For example, if the record-specific adjusted blacklist includes a list of names and a matched entity in that list is found in the unstructured data record, then that identified name will be removed and placed with the list specific tag of [name]. The addition of these tags provides context to the end-user about the type of data that was removed for better tuning and for increased legibility of the remaining de-identified data.

Figure 5:
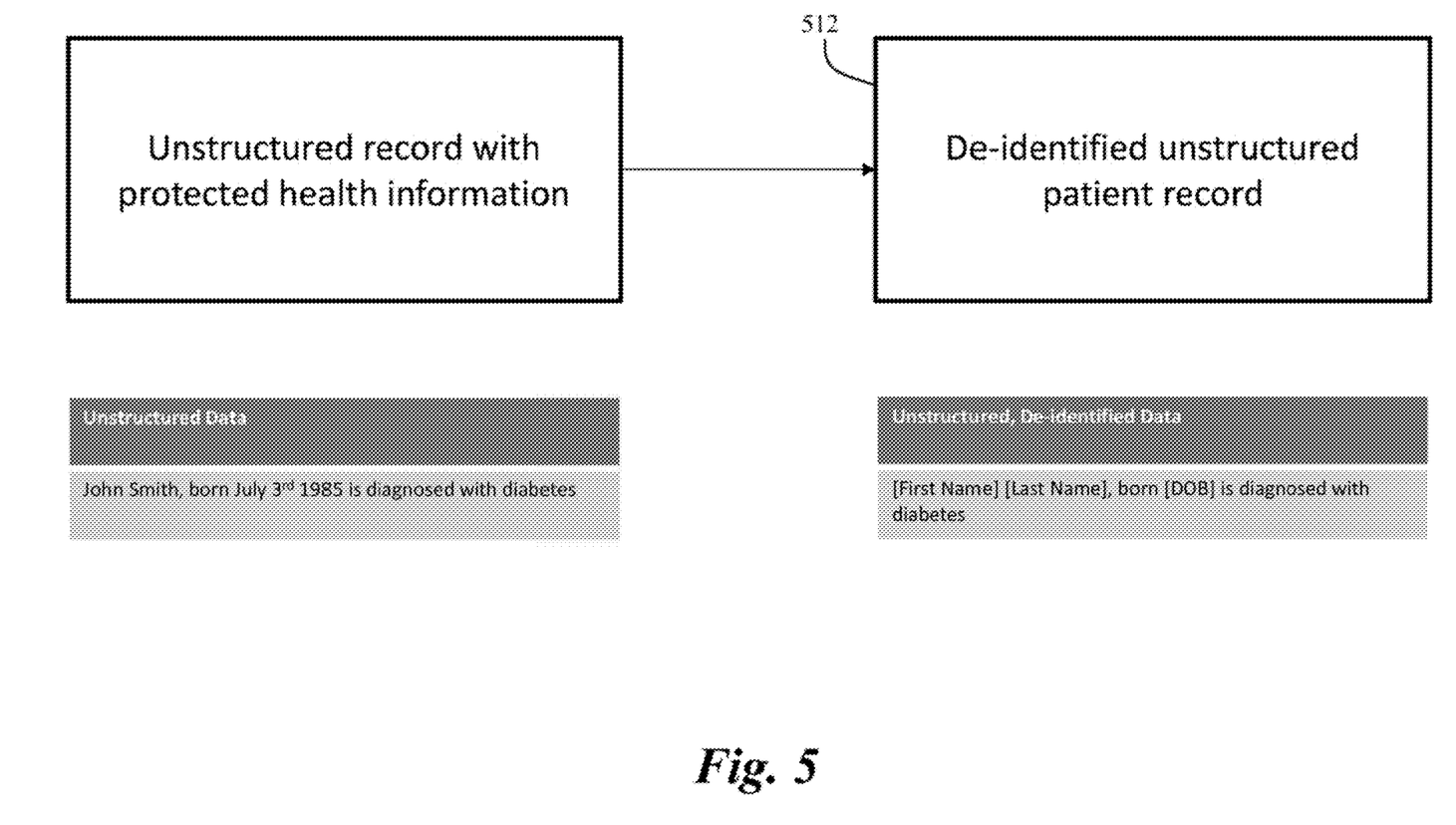
FIG. 5 is an illustration and example of how de-identified patient records are redacted, with the addition of case-type tags.

FIG. 5 is an illustrative example of how text from unstructured data is de-identified and removed and replaced with the case-specific tags. In particular, FIG. 5 depicts example textual data (including PHI) for an unstructured record and how that textual data is transformed into a de-identified unstructured patient record 512 through the processes 200, 300, and 400 depicted in FIGS. 2-4. The initial text for the unstructured data record includes "John Smith, born Jul. 3, 1985 is diagnosed with diabetes". This record is transformed by the de-identification process of the present invention to remove PHI of "John Smith" and "Jul. 3, 1985" and replace the removed text with case specific tags. The result of this transformation is the de-identified unstructured patient record 512 that includes "[First Name] [Last Name], born [DOB] is diagnosed with diabetes". This process takes the input of the unstructured data and outputs the de-identified data automatically following the steps provided in the processes discussed in greater detail in FIGS. 2-4. As would be appreciated by one skilled in the art, the example provided in FIG. 5 is for exemplary purposes only and not intended to limit the scope of the present invention to the terms/tags utilized therein. For example, the case-type tags can be made to give more context to the removed elements.

Figure 6:
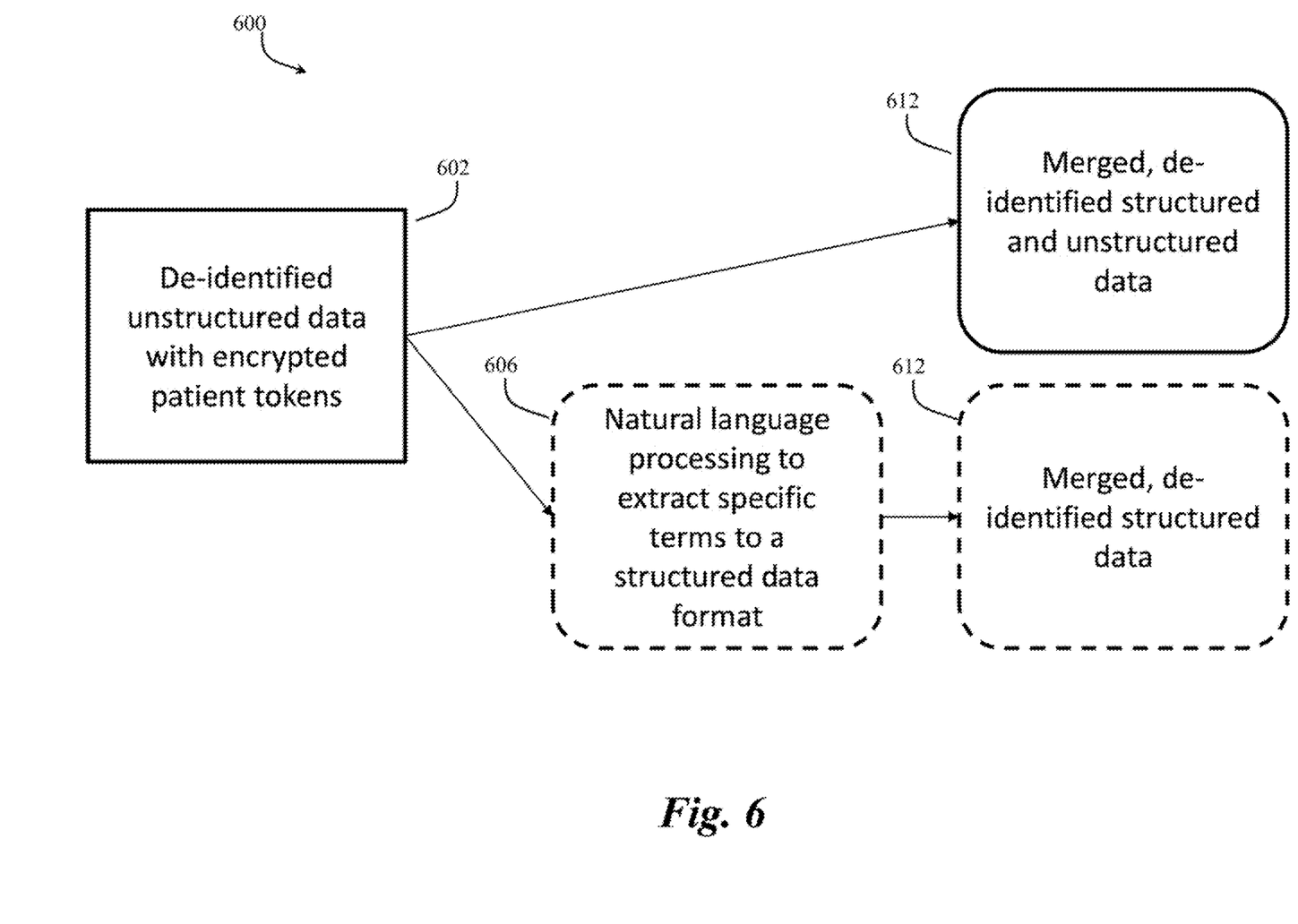
FIG. 6 is a flowchart illustrating the processes by which de-identified unstructured data can be merged with other de-identified datasets of structured data.

In accordance with an example embodiment of the present invention, the de-identified unstructured data records can be tokenized such that they can be matched with other de-identified data records. FIG. 6 illustrates the process 600 of linking de-identified unstructured data (as shown in FIGS. 2-4) with other data sets that have been de-identified through a different de-identification process (e.g., a process that works with structured data sets). For example, the de-identification of structured data sets can be provided by the de-deification process discussed in U.S. patent application Ser. No. 15/045,605 filed on Feb. 17, 2016 and U.S. Patent Application No. 62/561,032 filed on Sep. 20, 2017, incorporated herein by reference. The tokenizing process for de-identifying and tokenizing structured data sets can be used alongside the present invention to create an encrypted token for the unstructured data records of the present invention, as depicted in FIG. 6. In particular, using encrypted patient tokens 602, the de-identified unstructured data can be merged with other datasets, structured or unstructured, that have been similarly tokenized without any exposure to PHI or PII (e.g., in compliance with the Health Insurance Portability and Accountability Act (HIPAA) or other regulations). As depicted in FIG. 6, the de-identified data records created from unstructured data sources (as provided by the system 100 of the present invention) can be combined with de-identified data records created from structured data sources (as described in U.S. patent application Ser. Nos. 15/045,605 and 62/561,032). In accordance with an example embodiment of the present invention, the records can be combined by the merging module 120 in a similar method utilized in U.S. patent application Ser. Nos. 15/045,605 and 62/561,032. In short, the merging module 120 identifies the same token in both data sets and joins the records together to form merged data 612.

FIG. 6 also depicts an additional optional step in which the de-identified unstructured data processed by the present invention can undergo a subsequent step 606 of natural language processing to extract specific terms of interest and placing them in a structured data format. The case-type tags can assist in identifying elements of the unstructured data to be extracted. The resulting structured data can be then merged at step 612 with other structured data sets using the encrypted patient tokens.

Figure 7:
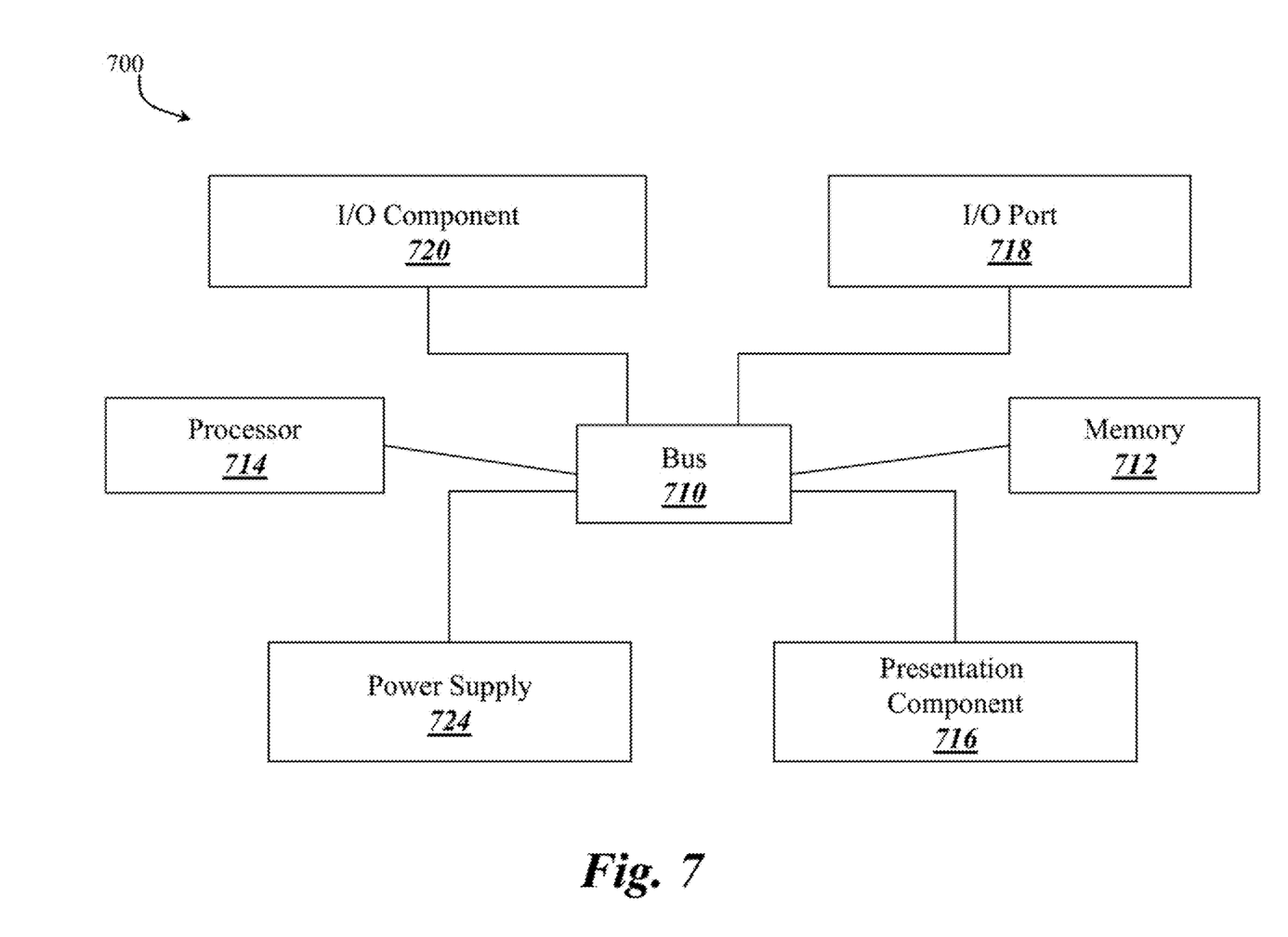
FIG. 7 is a diagrammatic illustration of a high-level architecture for implementing processes in accordance with aspects of the invention.

Any suitable computing device can be used to implement the computing devices 102, 122 and methods/functionality described herein and can be converted to a specific system for performing the operations and features described herein through modification of hardware, software, and firmware, in a manner significantly more than mere execution of software on a generic computing device, as would be appreciated by those of skill in the art. One illustrative example of such a computing device 700 is depicted in FIG. 7. The computing device 700 is merely an illustrative example of a suitable computing environment and in no way limits the scope of the present invention. A "computing device," as represented by FIG. 7, can include a "workstation," a "server," a "laptop," a "desktop," a "hand-held device," a "mobile device," a "tablet computer," or other computing devices, as would be understood by those of skill in the art. Given that the computing device 700 is depicted for illustrative purposes, embodiments of the present invention may utilize any number of computing devices 700 in any number of different ways to implement a single embodiment of the present invention. Accordingly, embodiments of the present invention are not limited to a single computing device 700, as would be appreciated by one with skill in the art, nor are they limited to a single type of implementation or configuration of the example computing device 700.

The computing device 700 can include a bus 710 that can be coupled to one or more of the following illustrative components, directly or indirectly: a memory 712, one or more processors 714, one or more presentation components 716, input/output ports 718, input/output components 720, and a power supply 724. One of skill in the art will appreciate that the bus 710 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 7 is merely illustrative of an exemplary computing device that can be used to implement one or more embodiments of the present invention, and in no way limits the invention.

The computing device 700 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 700.

The memory 712 can include computer-storage media in the form of volatile and/or nonvolatile memory. The memory 712 may be removable, non-removable, or any combination thereof. Exemplary hardware devices are devices such as hard drives, solid-state memory, optical-disc drives, and the like. The computing device 700 can include one or more processors that read data from components such as the memory 712, the various I/O components 716, etc. Presentation component(s) 716 present data indications to a user or other device. Exemplary presentation components include a display device, speaker, printing component, vibrating component, etc.

The I/O ports 718 can enable the computing device 700 to be logically coupled to other devices, such as I/O components 720. Some of the I/O components 720 can be built into the computing device 700. Examples of such I/O components 720 include a microphone, joystick, recording device, game pad, satellite dish, scanner, printer, wireless device, networking device, and the like.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method for de-identifying unstructured data within data sets, the method comprising:

initializing, using a computing device comprising a processor and memory, a blacklist dictionary having a structure that facilitates identification of personally identifiable information (PII) and protected health information (PHI) and that facilitates removal and replacement of PII and PHI with a case-type tag, and a whitelist dictionary comprising terms selected to remain in the data sets despite being included in the blacklist dictionary;

modifying, using the processor and a register module, the blacklist dictionary by removing terms included within the whitelist dictionary to create an adjusted blacklist dictionary;

augmenting, using the processor, the adjusted blacklist dictionary with a record-specific blacklist for each individual record within the data sets to create a record-specific adjusted blacklist dictionary;

scrubbing, using the processor and a de-identification engine, PII and PHI from each individual record utilizing the record-specific adjusted blacklist dictionary, the scrubbing comprising:

removing all elements within each individual record determined to be PII or PHI according to terms in the record-specific adjusted blacklist dictionary;

replacing removed elements with a case-type tag identifying a type of information being removed according to the record-specific adjusted blacklist dictionary; and repeating, using the de-identification engine, the scrubbing of PII and PHI comprising removing steps and replacing steps for each individual record within the data sets.

2. The method of claim 1, further comprising tokenizing and merging, using a merging module, each individual record in the data sets.

3. The method of claim 1, wherein the blacklist dictionary comprises standard terms and standard number formats to be removed from records within the data sets.

4. The method of claim 3, wherein the standard number formats comprise social security numbers, telephone numbers, URLs, zip codes, email addresses, IP addresses, dates, patient IDs, record numbers, and insurance IDs.

5. The method of claim 3, wherein the standard terms comprise cities, counties, first names, last names, prefixes, and medical terms.

6. The method of claim 1, wherein the record-specific adjusted blacklist dictionary comprises terms created from the PII or PHI present in specific individual records within the data sets.

7. The method of claim 1, further comprising tuning terms in the whitelist dictionary and the record-specific adjusted blacklist dictionary to adjust a level of de-identification of records within the data sets.

8. The method of claim 7, wherein the whitelist dictionary and the record-specific adjusted blacklist dictionary include a tunable list of names, birth dates, phone numbers, addresses and other forms of PII and PHI present in data store records or within the data sets.

9. The method of claim 7, wherein augmenting comprises adjusting the adjusted blacklist dictionary to include known PII and PHI terms, for an individual associated with an individual record, according to the record-specific adjusted blacklist dictionary, that are designated to be removed.

10. A system for de-identifying unstructured data within data sets, comprising:
  memory and a processor configured for accessing the data sets from data sources and parsing data within the data sets and identifying elements of unstructured data within the data sets and de-identifying unstructured data using a de-identification engine initializing a blacklist dictionary having a structure that facilitates identification of personally identifiable information (PII) and protected health information (PHI) and that facilitates removal and replacement of PII and PHI with a case-type tag, and a whitelist dictionary comprising terms selected to remain in the data sets despite being included in the blacklist dictionary, and comprising:
    a register module configured to modify the blacklist dictionary by removing terms included within the whitelist dictionary to generate an adjusted blacklist dictionary, and augmenting the adjusted blacklist dictionary with a record-specific blacklist for each individual record within the data sets to create a record-specific adjusted blacklist dictionary;
    a de-identification module configured to determine which unstructured elements are to be removed from each individual record of a data set by scrubbing PII and PHI from each individual record utilizing the record-specific adjusted blacklist dictionary, the scrubbing comprising:
      removing all elements within each individual record determined to be PII or PHI according to terms in the record-specific adjusted blacklist dictionary; and
      replacing removed elements with a case-type tag identifying a type of information being removed according to the record-specific adjusted blacklist dictionary;
    wherein the de-identification module repeats the scrubbing PII and PHI for each individual record within the data sets; and
  one or more user devices configured to receive input from one or more users by an input-output interface and communicate with the processor and the de-identification engine over a telecommunication network, providing functionality for the register module, de-identification module, and merging module that share a secured network connection.

11. The system of claim 10, further comprising a merging module configured to tokenize and merge each individual record in the data sets by identifying a same token in both data sets and join together matched to individual records in healthcare data sets without exposure of PHI or PII.

12. The system of claim 10, wherein the blacklist dictionary comprises standard terms and standard number formats to be removed from records within the data sets.

13. The system of claim 12, wherein the standard number formats comprise social security numbers, telephone numbers, URLs, zip codes, email addresses, IP addresses, dates, patient IDs, record numbers, and insurance IDs.

14. The system of claim 12, wherein the standard terms comprise cities, counties, first names, last names, prefixes, and medical terms.

15. The system of claim 10, wherein the record-specific adjusted blacklist dictionary comprises terms created from the PII or PHI present in specific individual records within the data sets.

16. The system of claim 10, further comprising tuning terms in the whitelist dictionary and the record-specific adjusted blacklist dictionary to adjust a level of de-identification of records within the data sets.

17. The system of claim 16, wherein the whitelist dictionary and the record-specific adjusted blacklist dictionary include a tunable list of names, birth dates, phone numbers, addresses and other forms of PII and PHI present in data source records or within the data sets.

18. The system of claim 16, wherein augmenting comprises adjusting the adjusted blacklist dictionary to include known PII and PHI terms for an individual associated with an individual record, according to the record-specific adjusted blacklist dictionary, that are designated to be removed.

* * * * *